Dec. 13, 1960
O. O. DUNHAM
CHRYSANTHEMUM PLANT
Filed July 27, 1959
Plant Pat. 2,001
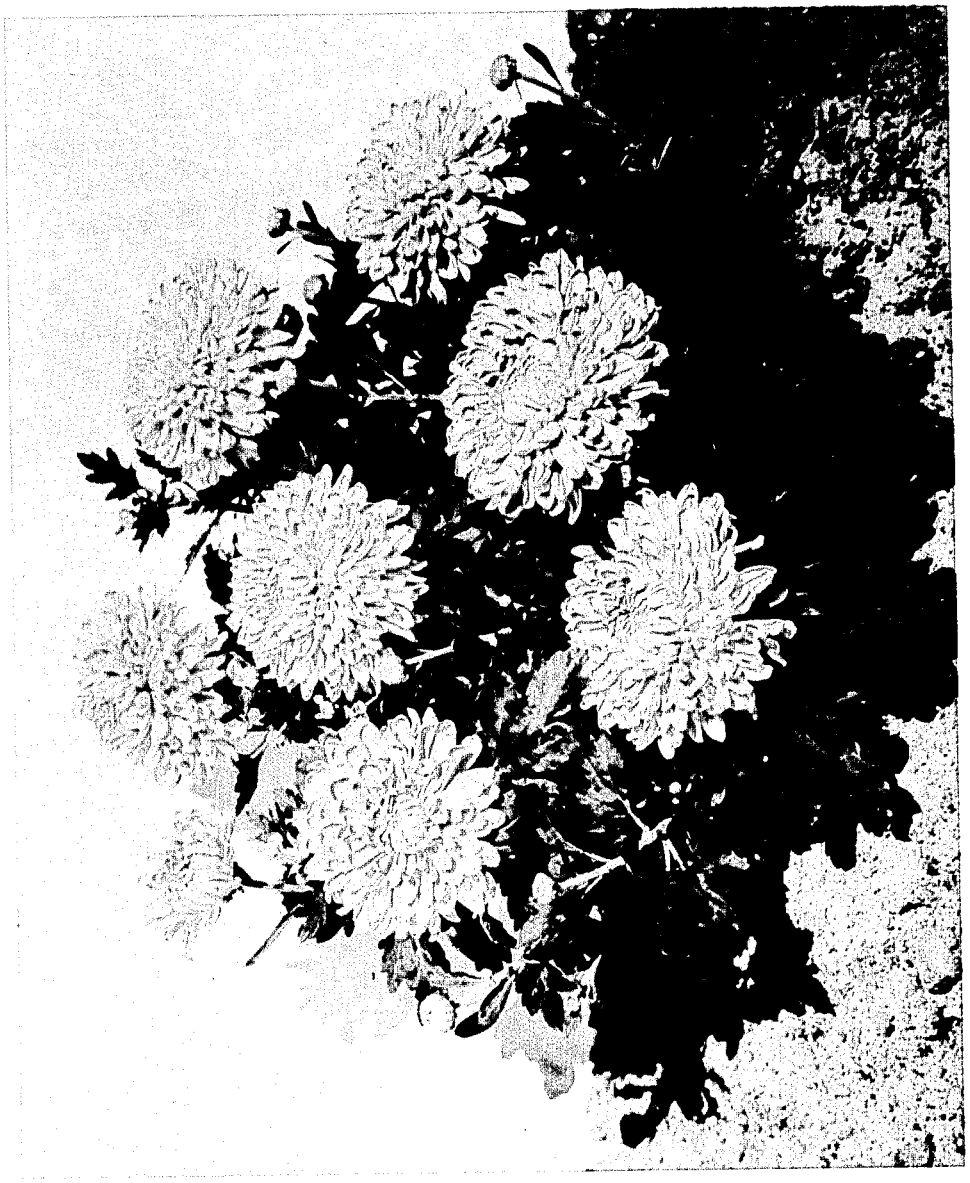
Inventor
O. O. Dunham
by Robbe Robb
attorneys United States Patent Office Plant Pat. 2,001
Patented Dec. 13, 1960

2,001

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,943

1 Claim. (Cl. 47—60)

My present invention comprises a new and distinct variety of chrysanthemum plant which is the result of crossing the variety "Attraction" (unpatented), which is one of my own introductions, and the unpatented variety which I designate as "No. 5350."

The object of my invention has been to produce a new variety of chrysanthemum of the indicum type which will have a more compact habit and early flowering as well as continuous flowering with better flower color and foliage than prior plants, together with a somewhat lighter general color than the parent "Attraction."

I have carried on an extensive program of development in order to produce new varieties of chrysanthemums and as a result of such program which I have been conducting involving careful selection and cross-breeding, a number of varieties have been produced of the indicum type which have some of the desirable characteristics of two basically different chrysanthemum types, namely the American garden chrysanthemum and the English early chrysanthemum. The desirable characteristics of the English early chrysanthemums have been brought forth in this program involving the continuous nature as against some of the irregular flowering which is somewhat characteristic of that type. The American garden chrysanthemum on the other hand flowers continuously but flowers only over a short period of time. The combining of the desirable characteristics of both general types will be apparent as producing different chrysanthemums and as is true in this particular instance.

The result of the specific hybridization previously mentioned has been to produce my present new and distinct variety of chrysanthemum plant, which is characterized by the strong pink to deep pink color of its blooms, the very double arrangement of its petals, the vigorous, more compact habit of growth, more abundant, larger foliage, large size blooms, and early, continuous and long blooming period.

More specifically, the blooms of my new variety are of a strong pink to deep pink color (Nickerson Color Fan published by Munsell Color Company). As grown in the vicinity of Niles, Michigan, under uniform culture, plants of my new variety have grown to an average to medium height of fourteen to twenty inches.

My new variety bears a closer resemblance to the seed parent "No. 5350" than to the pollen parent "Attraction" but in any event my new variety differs from both of its parents and some other known varieties in many respects.

In comparing the color of the bloom of my new variety with the color of the blooms of the variety "Attraction" it is found that the blooms of the latter are more of the moderate pink to strong yellowish pink (Munsell Hue 5R 8/16 to 7/9) in contrast to the colors of the instant variety which is of the strong pink to deep pink (Munsell Hue 2.5R 7/8 to 6/11).

The blooms of the instant variety are larger than the blooms of either of the parents and may be classified as being very large, being of an average size of five inches when fully expanded. The petal arrangement in my new variety is also very double and innumerable petals are found under normal conditions. The petal arrangement in my new variety being very double, there is some difficulty in finding the stamens for further breeding and in fact the stamens in my new variety are rare and small.

Under conditions of culture previously mentioned which have taken place in the region of Niles, Michigan, my new variety has commenced blooming early in September and has bloomed profusely and continuously until a killing frost. In this particular instance a very light frost tends to intensify colors of such blooms.

My new variety has been asexually reproduced by cuttings, in the vicinity of Niles, Michigan.

The buds of my new variety are large and short with flat top, and when they begin to unfurl, are of a deep purplish pink washed with a somewhat deeper purplish pink, the bud and petals gradually lightening during the course of opening.

It should be noted that the foliage produced in this particular variety, is more abundant, darker more brilliant green and of somewhat larger size than the parent plants.

My new variety has been found to retain its distinctive characteristics through successive asexual reproductions.

The accompanying drawing forming a part hereof shows a typical plant of my new variety of chrysanthemum.

The following is a detailed description of my new variety of chrysanthemum plant, the color references being to the Nickerson Color Fan published by Munsell Color Company:

Parentage: Seedling.
- *Seed parent.*—No. 5350 (unpatented).
- *Pollen parent.*—"Attraction" (unpatented).

Classification: Botanic—*Chrysanthemum indicum.*

*Flower*

Blooming habit: Blooms profusely and continuously from early in September until a killing frost. Observations were made in Niles, Michigan in September.

Bud:
- *Size.*—Large.
- *Form.*—Short with flat top. Not affected by hot or wet weather. Sepals of no consequence.
- *Color.*—When petals begin to unfurl—5RP 6/10 deep purplish pink washed with 7.5RP 6/12 deep purplish pink. When half blown: inside of petals—5RP 5/10 moderate purplish-red washed with 7.5RP 5/12 strong purplish red; reverse of petals—5RP 8/5 light purplish pink.
- *Peduncle.*—Very long.
- *Aspect.*—Rough.
- *Color.*—Medium green.
- *Strength.*—Stiff; erect.
- *Opening.*—Bud opens well—somewhat affected by adverse conditions.

Bloom:
- *Size.*—Very large. Average size when fully expanded 5 inches (disbudded).
- *Borne.*—Clusters—irregular.
- *Stems.*—Medium; strong.
- *Form.*—When first open—flat. Permanence—retains its form to the end.
- *Petalage.*—Very double. Number of petals under normal conditions—innumerable.
- *Color.*—Center of flower 5R 6/11 Munsell Hue 5 Red. Outer petals 2.5R 8/5 Munsell Hue 2.5 Red. Base of Petals (singlet)—2.5R 7/8 Munsell Hue 2.5 Red. Inside of petals—2.5R 7/8 Munsell Hue 2.5 Red. Reverse of petals—2.5R 9/3 Munsell Hue 2.5 Red. General tonality from a distance—between 2.5R 7/8 and 2.5R 6/11 Munsell Hue 2.5 Red.

*Discolorations.*—General tonality at end of: First week—retains same color. Second week—retains somewhat same color. Third week—retains somewhat same color.

Petals:

*Texture.*—Thin. Bleaches in hot weather. Affected by fungus infection in wet weather.

*Appearance.*—Inside—velvety. Outside—satiny.

*Form.*—Pointed.

*Arrangement.*—Imbricated.

*Persistence.*—Hang on and dry.

*Fragrance.*—None.

*Lastingness.*—On the plant—very long. As cut flower—long.

Genital organs:

*Stamens, anthers.*—Small; few. Color—yellow. Arrangement—regular around styles.

*Stamens, filaments.*—Short. Color—white.

*Styles.*—Columnar. Length—short.

*Stigmas.*—White in color.

*Ovaries.*—All enclosed in calyx.

Fruit: Variety is fertile with own pollen.

*Form.*—Oblong shaped.

*Aspect.*—Rough.

*Color at maturity.*—Brownish grey.

*Plant*

Form: Bush.

Growth: Vigorous; dwarf; branching; compact.

Foliage:

*Size.*—Large.

*Quantity.*—Abundant.

*Color.*—New foliage: upper side—normal green; under side—light green. Old foliage: upper side—dark green; under side—dark green.

*Shape.*—Three lobed.

*Texture.*—Upper side—smooth; flat. under side—velvety. Ribs and veins—ordinary.

*Edge.*—Smooth.

*Leaf stem.*—Green in color. Under side—smooth.

*Stipules.*—short.

*Disease resistance.*—Under certain conditions susceptible to mildew.

I claim:

A new and distinct variety of chrysanthemum plant substantially as herein disclosed, characterized as to novelty by the strong pink to deep pink color of its blooms, the very double arrangement of its petals, vigorous, more compact habit of growth, more abundant, larger foliage, the large size of its blooms and the early, continuous and long blooming period.

No references cited.